(12) United States Patent
Burckhardt et al.

(10) Patent No.: US 6,215,029 B1
(45) Date of Patent: Apr. 10, 2001

(54) PROCESS FOR THE PREPARATION OF HALOGENATED HYDROXYDIPHENYL COMPOUNDS

(75) Inventors: Urs Burckhardt, Basel (CH); Armando Di Teodoro, Rheinfelden (DE); Werner Hölzl, Eschentzwiller (FR); Dieter Reinehr, Kandern (DE); Rudolf Zink, Therwil (CH); Hanspeter Sauter, Schopfheim; Uwe Gronde, Rheinfelden, both of (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/328,744

(22) Filed: Jun. 9, 1999

Related U.S. Application Data

(63) Continuation of application No. 09/019,377, filed on Feb. 5, 1998, now abandoned.

(30) Foreign Application Priority Data

Feb. 5, 1997 (EP) .................................................. 97810064

(51) Int. Cl.$^7$ .................................................. C07C 41/01
(52) U.S. Cl. .................... 568/639; 568/628; 568/637; 568/638; 560/131; 560/138
(58) Field of Search .................... 568/628, 637, 568/638, 639, 837, 838; 560/131, 138

(56) References Cited

U.S. PATENT DOCUMENTS

| | | | |
|---|---|---|---|
| 3,506,702 | 4/1970 | Model | 260/613 |
| 3,576,843 | 4/1971 | Model et al. | 260/479 |
| 4,564,712 | 1/1986 | Kukertz et al. | 568/635 |
| 4,950,809 | 8/1990 | Gubelmann | 568/741 |
| 5,012,017 | 4/1991 | Orvik et al. | 568/803 |

FOREIGN PATENT DOCUMENTS

| | | |
|---|---|---|
| 1 493 776 | 7/1969 | (DE) . |
| 2117826 | 10/1971 | (DE) . |
| 0 384 043 | 8/1990 | (EP) . |
| 99/10310 | 3/1999 | (WO) . |

OTHER PUBLICATIONS

"The Merk Index, 12$^{th}$ Ed.", (1996), p. 1646, No. 9790.

Atkinson et al., J. Med. Chem., 26(10), pp. 1353–1360 (1983).

Advanced Organic Chemistry, Reactions, Mechanisms, and Structure, 3$^{rd}$ Ed., pp. 485, 589 and 990 (1985).
Lancaster, 93/94, Entries 5784,0286 and 6150 (1994).
Harris et al, Journal of Medicinal Chemistry, vol. 25, No. 7, pp. 855–858, 1982.*

* cited by examiner

Primary Examiner—Sreeni Padmanabhan
(74) Attorney, Agent, or Firm—Kevin T. Mansfield

(57) ABSTRACT

A process for the preparation of halohydroxydiphenyl compounds useful for protecting organic materials and articles from microorganisms, of the formula

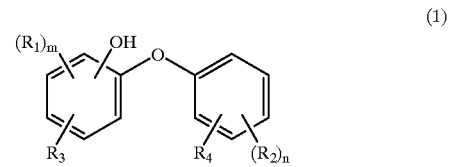

by acylation of a halogenated benzene compound (first stage), etherification of the acylated compound with a halogenated phenol compound (second stage), oxidation of the etherified compound (third stage) and hydrolysis of the oxidized compound in a fourth stage, according to the following reaction scheme:

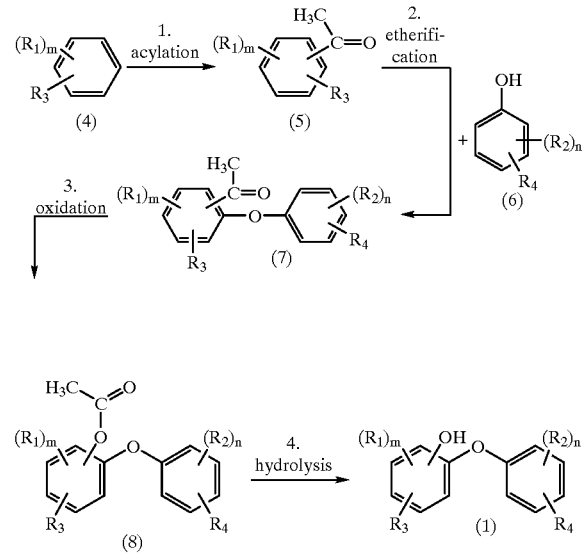

in which $R_1$ and $R_2$ independently of one another are F, Cl or Br; $R_3$ and $R_4$ independently of one another are hydrogen; or $C_1$–$C_4$alkyl; m is 1 to 3; and n is 1 or 2.

13 Claims, No Drawings

PROCESS FOR THE PREPARATION OF HALOGENATED HYDROXYDIPHENYL COMPOUNDS

This is a continuation of application Ser. No. 09/019,377, filed on Feb. 5, 1998, now abandoned.

The present invention relates to the preparation of halogenated hydroxydiphenyl compounds of the formula

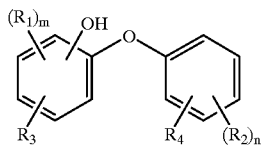

in which $R_1$ and $R_2$ independently of one another are F, Cl or Br;
$R_3$ and $R_4$ independently of one another are hydrogen; or $C_1$–$C_4$alkyl;
m is 1 to 3; and
n is 1 or 2;

and to the use of these compounds as disinfectants for protecting organic materials from microorganisms.

The preparation of halogenated hydroxydiphenyl compounds, in particular of 2-hydroxy-2',4,4'-trichlorodiphenyl ether (Triclosan; compound of the formula (3)) is usually carried out by diazotisation and subsequent hydrolysis of 2-amino-2',4,4'-trichlorodiphenyl ether (TADE; compound of the formula (2)).

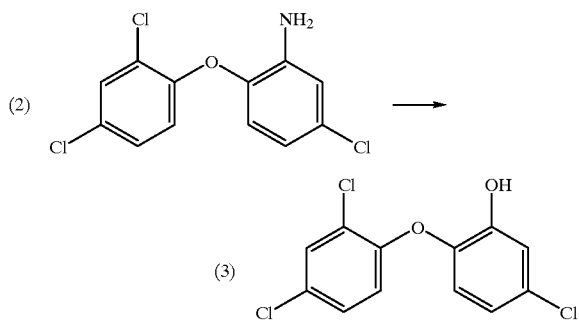

However, the yield in this preparation method is unsatisfactory, as various competitive chemical reactions can take place.

The present invention is therefore based on the object of finding an economical process for the preparation of halohydroxydiphenyl compounds, in which the undesired side reactions are suppressed.

The object is achieved according to the invention by a four-stage reaction, in which in the first stage a halogenated benzene compound is acylated, in the second stage the acylated compound is etherified using a halogenated phenol compound, in a third stage the etherified compound is oxidized and in a fourth stage the oxidized compound is hydrolysed, according to the following reaction scheme:

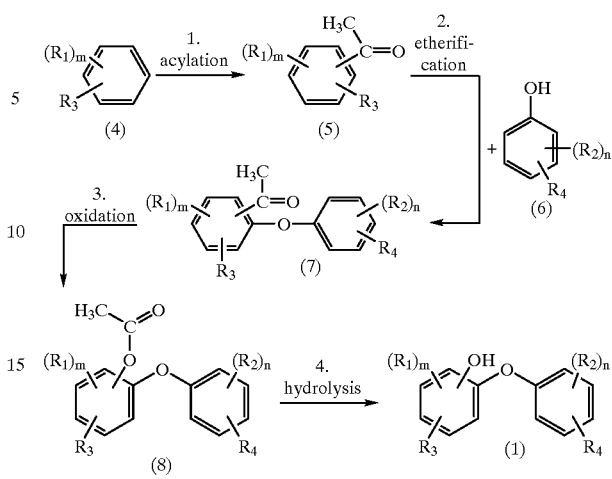

In the above scheme, $R_1$, $R_2$, $R_3$, $R_4$, m and n are as indicated in formula (1).

In the first reaction step (acylation reaction), compounds of the formula (5) are prepared. Usually, this reaction is carried out in the presence of a Lewis acid, e.g. aluminium halide, in particular aluminium chloride. The Lewis acid is in this case employed in a 1 to 3, preferably 1.25 to 2, molar amount, based on the halogenated compound of the formula (5). A possible acylating reagent for this reaction is an acyl halide, in particular acetyl chloride.

$C_1$–$C_4$alkyl is preferably a straight-chain or branched alkyl radical, e.g. methyl, ethyl, n-propyl, isopropyl, n-butyl, sec-butyl or tert-butyl.

The Lewis acid and acylating reagent are preferably employed in equimolar amounts. The reaction is carried out in the solvents customary for Friedel-Crafts reactions, e.g. methylene chloride or ethylene chloride. The reaction time for this reaction stage plays a minor part and can vary within a wide range, from, for example, 1 to 18 hours.

In the second reaction stage, the compounds of the formula (7) are prepared. The etherification of the free OH group of the halogenated phenol compound of the formula (6) is usually carried out in alkaline medium using a strong organic or preferably inorganic base, e.g. NaOH or KOH, and in the presence of a copper catalyst and an inert organic solvent, e.g. toluene or a xylene isomer mixture. The reaction times for this reaction step are usually 1 to 24 hours, preferably 2 to 10 hours; the temperature ranges from 80 to 250° C., preferably 100 to 170° C.

In the third reaction stage (oxidation), compounds of the formula (8) are prepared. The oxidation of the acyl compound of the formula (7) to the compound of the formula (8) (Baeyer-Villiger oxidation) can be carried out using various oxidizing agents. Suitable oxidizing agents are, for example:

a mixture of dilute peracetic acid and acetic anhydride in the presence of a catalytic amount of perchloric acid;
m-chloroperbenzoic acid (MCPBA) in water;
diperoxydodecanedioic acid (DPDDA);
a mixture of dilute peracetic acid and acetic anhydride and sulfuric acid;
perbenzoic acid (PBA)
a mixture of sodium borate and trifluoroacetic acid;
a mixture of formic acid, hydrogen peroxide, acetic anhydride, phosphorus pentoxide and acetic acid;
a mixture of acetic acid, hydrogen peroxide, acetic anhydride and phosphorus pentoxide;
a mixture of $K_2S_2O_8$, sulfuric acid and a 1:1 water/methanol mixture;

a mixture of acetic acid and the potassium salt of monoperoxymaleic acid;

a mixture of trichloromethylene, the potassium salt of monoperoxymaleic acid and sodium hydrogen sulfate;

a mixture of maleic anhydride, acetic anhydride, hydrogen peroxide and trichloromethane;

a mixture of maleic anhydride, a urea-hydrogen peroxide complex and acetic acid;

magnesium monoperphthalate;

a mixture of acetic anhydride, sulfuric acid and $H_2O_2$;

a mixture of dichloroacetic acid and $H_2O_2$.

m-Chloroperbenzoic acid (MCPBA), a mixture of sodium borate and trifluoroacetic acid or a mixture of acetic anhydride and $H_2O_2$ is preferably used for the oxidation. If desired, a commercially available wetting agent can additionally be added to the oxidizing agent. The reaction times lie in a wide range and range from about 0.5 to about 15 hours, preferably 1 to 8 hours. The reaction temperature ranges from −20 to about 100° C., preferably from 0 to about 85° C.

The subsequent hydrolysis to give the desired halohydroxydiphenyl ether of the formula (1) proceeds quantitatively in the acidic or alkaline medium.

The process according to the invention preferably relates to the preparation of halohydroxydiphenyl compounds of the formula (1), in which $R_1$ and $R_2$ are Cl.

Particularly preferred compounds of the formula (1) are those in which m is 2 and n is 1 or m and n are 1.

Very particularly preferred compounds of the formula (1) have the formula

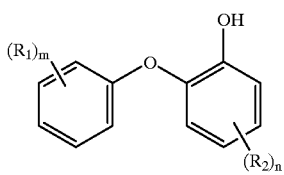

(9)

in which $R_1$ and $R_2$ are Cl; and m is 2 and n is 1;

and in particular the compound of the formula

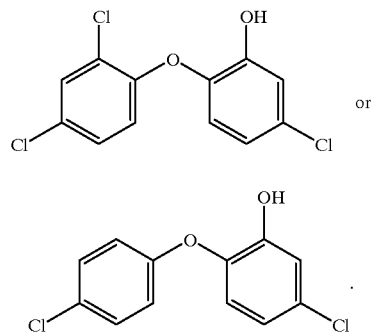

(10)

or (11)

The acyl compounds formed in the 2nd reaction stage (Ullmann condensation) in some cases are novel compounds. These are the compounds of the formula

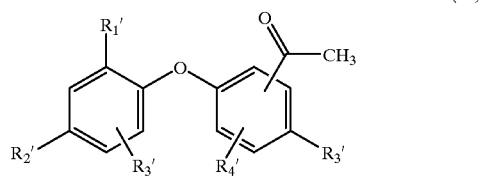

(12)

in which $R_1'$, $R_2'$ and $R_3'$ independently of one another are F, Cl or Br; and $R_4'$ and $R_5'$ independently of one another are hydrogen; or $C_1$–$C_5$alkyl.

In particular, novel compounds of the formula

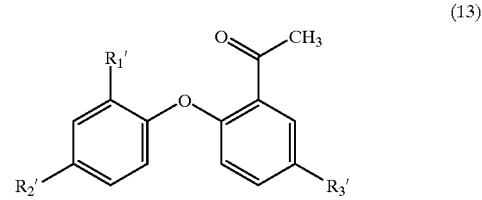

(13)

are preferred in which $R_1'$, $R_2'$ and $R_3'$ independently of one another are F, Cl or Br.

The halogenated hydroxydiphenyl compounds prepared according to the invention are insoluble in water, but soluble in dilute sodium hydroxide and potassium hydroxide solution and in virtually all organic solvents. Owing to these solubility requirements, their applicability for the control of microorganisms, in particular of bacteria, and as disinfectants for protecting organic materials and articles from attack by microorganisms is very versatile. Thus they can be applied to these in diluted or undiluted form, for example, together with wetting or dispersing agents, e.g. as soap or syndet solutions for the disinfection and cleaning of human skin and hands, in dental hygiene compositions and hard articles.

The following examples illustrate the invention without restricting it thereto.

PREPARATION EXAMPLES

Example 1

Preparation of 2,5-dichloroacetophenone (first reaction stage

Reaction scheme:

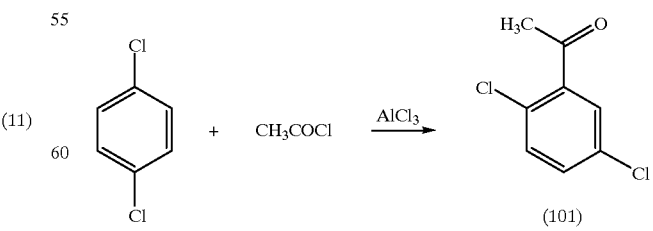

(101)

147 g (1.0 mol) of p-dichlorobenzene are completely melted at 60° C. in an apparatus having an attached dropping funnel, stirrer and reflux condenser. 120 g (0.9 mol) of anhydrous AlCl₃ are added to the melt. 39.3 g (0.5 mol) of acetyl chloride are then added dropwise to the readily stirrable suspension at 60° C. in the course of about 1 hour, a clear solution slowly resulting. After heating to 110° C., the mixture is stirred at this temperature for 7 hours. After cooling to room temperature, the brown reaction mass is hydrolysed by cautious decantation onto a mixture of 200 ml of water and 200 g of ice. The temperature of the mixture is kept between 30 and 40° C. during the hydrolysis by external cooling. After separation of the phases, the lower, organic phase is washed with 400 ml of water and, after fresh phase separation, subjected to fractional distillation. The aqueous phases are discarded.

Yield: 66 g of 2,5-dichloroacetophenone (70% of theory, based on acetyl chloride)

Example 2

Preparation of 1-(5-chloro-2-(2,4-dichlorophenoxy) phenylethanone (second reaction stage)

Reaction scheme:

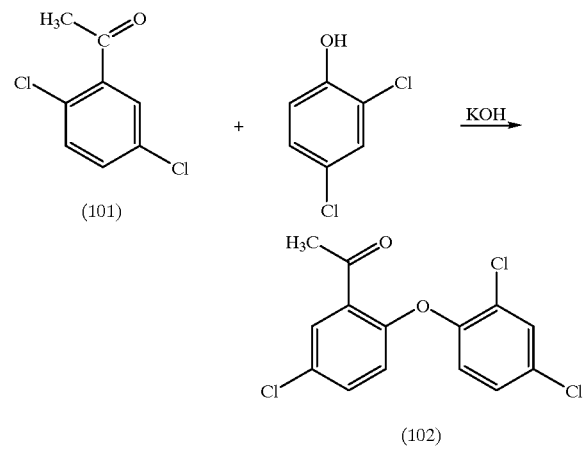

163 g of 2,4-dichlorophenol are initially introduced together with 22.0 g of 85% KOH and 167 ml of xylene isomer mixture. The whole is heated to reflux and the water is removed by azeotropic distillation. The red-brown, clear solution is then cooled to 100° C., treated with 189 g of 2,5-dichloroacetophenone (compound of the formula (101)) and 0.8 g of basic copper carbonate, heated to 140° C. and stirred at this temperature within 8 hours. In the course of this, the reaction solution turns dark red-brown and a white precipitate deposits, which is filtered off. After distilling off the largest part of the xylene in a gentle water-jet vacuum, a fraction of 208 g is obtained, which in addition to the starting products 2,4-dichlorophenol and 2,5-dichloroacetophenone additionally contains some xylene (b.p. 30–85° C./0.5–1 mm Hg). 82 g of a second, slightly yellowish fraction (b.p. 165–175° C./1 mm Hg) of the compound of the formula (102) are obtained, corresponding to a yield of 82% of theory, based on KOH employed (m.p.=91° C.).

| Analysis for C₁₄H₉Cl₃O₂ (MW = 315.58): | | | | |
|---|---|---|---|---|
| | C | H | Cl | O |
| Calculated [%] | 53.28 | 2.87 | 33.7 | 10.14 |
| Found [%] | 53.31 | 2.85 | 33.37 | 10.31 |

Example 3

Preparation of 1-(5-chloro-2-(4-chlorophenoxy)phenyl) ethanone (2nd reaction stage)

The procedure is as described in Example 2, but using 128.6 g of 4-chlorophenol instead of 163 g of dichlorophenol.

After a reaction time of 2 hours at 140° C. and subsequent working up as described in Example 2, a main fraction of 91 g (b.p. 112° C.–173° C./1 mm Hg) is obtained, after a preliminary fraction of 223 g (b.p. 30–112° C./1 mm Hg), which in addition to the starting material 2,5-dichloroacetophenone contains more than 80% of the reaction product of the formula

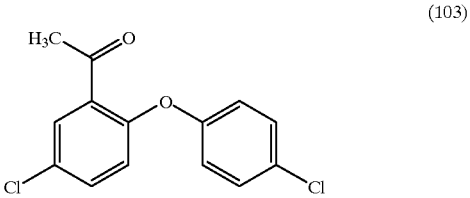

which on cooling solidifies to give a white powder (m.p.= 64° C.).

| Analysis for C₁₄H₁₀Cl₂O₂ (MW = 281.14): | | | | |
|---|---|---|---|---|
| | C | H | Cl | O |
| Calculated [%] | 59.81 | 3.59 | 25.22 | 11.38 |
| Found [%] | 59.74 | 3.48 | 25.49 | 11.29 |

Example 4

Preparation of 5-chloro-2-(2,4-dichlorophenoxy)phenol by Baeyer-Villiger oxidation with m-chloroperbenzoic acid (MCPBA) (third and fourth reaction stage)

Reaction scheme

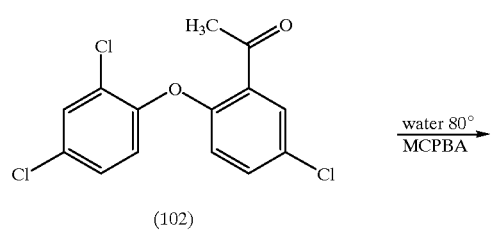

-continued

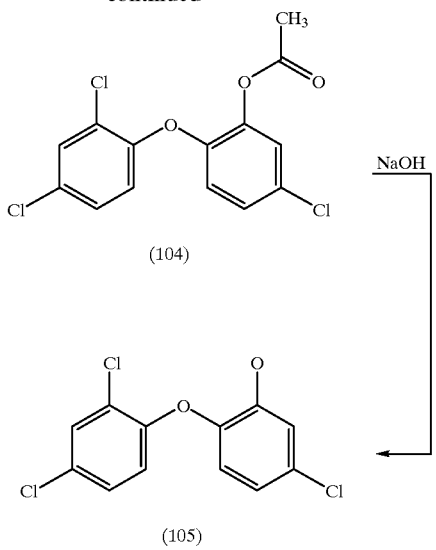

(104)

(105)

6.3 g of the acetyl compound of the formula (102) are suspended in 40 ml of deionized water at 20° C. 9.8 g of m-chloroperbenzoic acid (MCPBA) are scattered in and the mixture is heated with stirring. A resin/water phase is formed from 52° C.; the mixture is heated to about 80° C. and this temperature is maintained for 6 hours.

The mixture is treated with 0.5 g of sodium hydrogen sulfite to eliminate excess peroxide. Two clear phases are obtained by addition of 50 ml of ethylene chloride and 4 g of 10N NaOH. The water phase having a pH of about 12 is separated off; the solvent phase is washed with water until neutral. After distillation of the solvent, 5.5 g of crystallizing compound of the formula (104) remain (phenol ester intermediate).

For hydrolysis, the phenol ester is dissolved in 50 ml of ethylene chloride and 10 ml of 5N sodium hydroxide solution. The solution is heated to 70–73° C., this temperature is maintained for 15 minutes, then the pH is adjusted to about 4 using acetic acid and the phases are separated. After removal of the solvents, 4.9 g of beige-coloured crude product of the formula (105) are obtained.

After clarifying filtration and recrystallization from petroleum ether 80/110, the pure product is obtained in colourless crystals and with a melting point of 56 to 57° C.

Example 5
Preparation of 5-chloro-2-(2,4-dichlorophenoxy)phenol by Baever-Villiger oxidation with NaBO₃ (third and fourth reaction stage)

6.3 g of the acetyl compound of the formula (102) are suspended in 20 ml of trifluoroacetic acid and the suspension is treated at 20° C. with 9.3 g of sodium perborate tetrahydrate. It is heated to 40° C. and this temperature is maintained for 90 minutes with good stirring. After hydrolysis of the phenol ester formed and working up analogously to Example 4, 5.4 g of crude product of the formula (105) are obtained.

Example 6
Preparation of 5-chloro-2-(2,4-dichlorophenoxy)phenol by Baever-Villiger oxidation with acetic anhydride/H₂O₂

18 ml of acetic anhydride are mixed at −5° C. with 4.5 ml of 98% sulfuric acid. 4.2 ml of 30% hydrogen peroxide are added dropwise with very vigorous stirring at −5 to −3° C. in the course of 25 minutes. The milky emulsion is treated at −5° C. with 12.5 ml of methylene chloride, a clear solution being formed.

This is then added with very vigorous stirring in the course of 3 minutes to a mixture of 7.9 g of the acetyl compound of the formula (102), 15 ml of methylene chloride, 18 ml of 100% acetic acid and 13.5 ml of 98% sulfuric acid, at a temperature of 0 to −5° C.

The reaction mixture is two-phase and dark. The reaction is kept at 0 to 5° C. for one hour, then at 10° C. for 4 hours and at 15° C. for 1 hour. It is finally allowed to react to completion at 20° C. for 20 hours, the intermediately formed phenol ester of the formula (104) also being partially hydrolysed to the phenol derivative of the formula (105).

After destruction of the excess hydrogen peroxide, the methylene chloride is distilled out. For complete hydrolysis, the temperature is kept at 100° C. for 4 hours. The product is recovered via methylene chloride extraction. After distillation of the solvent, an oily residue of 7 g of the crude product of the formula (105) remains, which after customary purification yields the product with a melting point of 56 to 57° C.

Example 7
Preparation of 5-chloro-2-(4-chlorophenoxy)phenol (third and fourth reaction stage)

Reaction scheme:

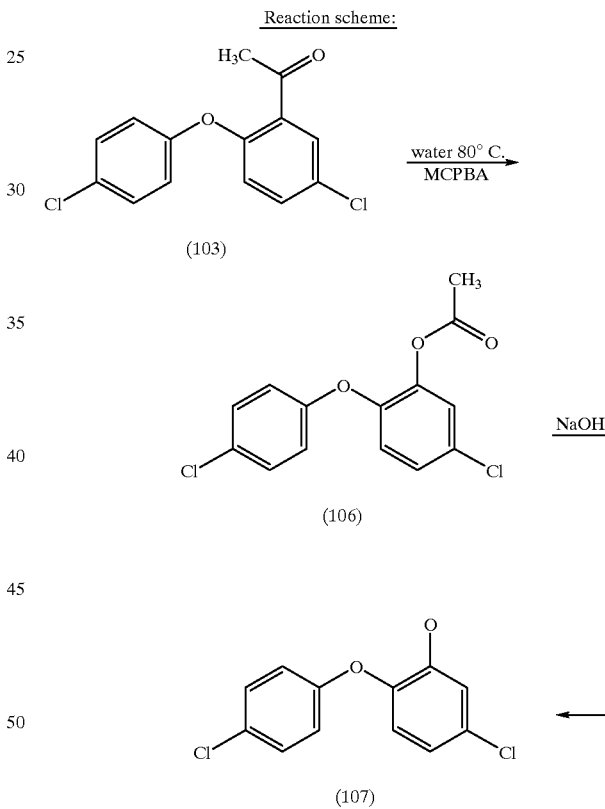

(103)

(106)

(107)

14 g of the acetyl compound of the formula (103) are suspended in 100 ml of deionized water at 20° C. using a wetting agent. 29 g of 70% 3-chloroperbenzoic acid (MCPBA) are scattered in and the mixture is heated with stirring. A resin/water phase is formed from 52° C.; the mixture is heated to about 80° C. and kept at this temperature for 7 hours.

It is treated with 0.5 g of sodium hydrogen sulfite to eliminate excess peroxide. Two clear phases are obtained by addition of 50 ml of xylene isomer mixture and 9 g of 10N NaOH. The water phase having a pH of about 12 is separated off; the solvent phase comprising the compound of the formula (106) is washed with water until neutral.

To hydrolyse the ester, the xylene phase is treated with 24 g of 10% NaOH and stirred under reflux (about 95° C.) for 5 hours. The xylene phase is then separated off and the pale brown water phase is adjusted to a pH of about 3 using 4 g of 34% hydrochloric acid at 25° C. In the course of this, the product precipitates in sandy, beige-coloured form and, after filtration, can be thoroughly washed with water on the suction filter. After drying, 5 g of the crude product of the formula (107) having a melting point of 73 to 74° C. are obtained.

After recrystallization from petroleum ether 80/110, the pure substance is obtained in colourless crystals having a melting point of 74 to 74.5° C.

Examples 8 to 14

The following compounds are obtainable analogously to the preparation process described above:

| Example | Acetyl compound | Final product |
|---|---|---|
| 8 | | |
| 9 | | |
| 10 | | |
| 11 | | |
| 12 | | |
| 13 | | |

-continued

| Example | Acetyl compound | Final product |
|---|---|---|
| 14 | 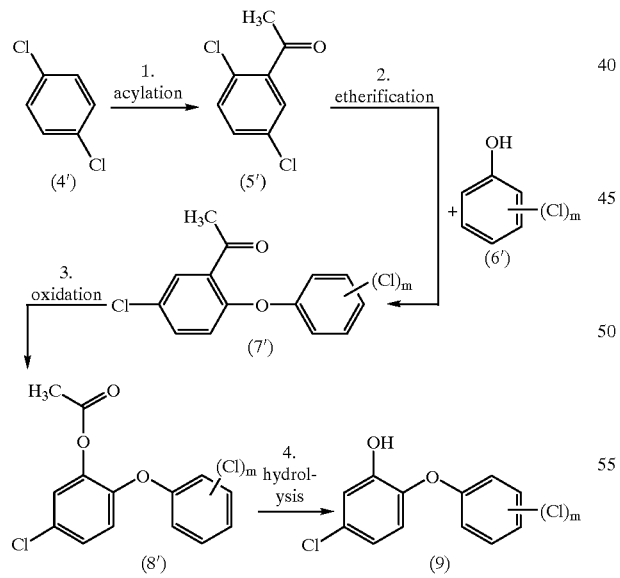 | |

What is claimed is:

1. A process for the preparation of a chlorinated hydroxy-diphenyl compound of the formula (9)

by acylation of a chlorinated benzene compound (first stage), etherification of the acylated compound with a chlorinated phenol compound in the presence of a strong organic or inorganic base, wherein the molar ratio of the base to the chlorinated phenol is from 0.5:1 to 0.3:1, a copper catalyst and an inert organic solvent selected from the group consisting of toluene, xylene and a xylene isomer mixture (second stage), oxidation of the etherified compound (third stage) and hydrolysis of the oxidized compound in a fourth stage, according to the following reaction scheme:

wherein m is 1 or 2.

2. A process according to claim 1, wherein in the acylation reaction (first stage) the compound of the formula (5') is formed.

3. A process according to claim 1, wherein the acylation reaction (first stage) is carried out in the presence of a Lewis acid.

4. A process according to claim 1, wherein acetyl chloride is used for the acylation reaction.

5. A process according to claim 1, wherein in the etherification (second stage) the compound of the formula (7') is formed.

6. A process according to claim 1, wherein in the oxidation (third stage) the compound of the formula (8') is formed.

7. A process according to claim 1, wherein the oxidation is carried out in the presence of m-chloroperbenzoic acid.

8. A process according to claim 1, wherein the oxidation is carried out in the presence of a mixture of sodium borate and trifluoroacetic acid.

9. A process according to claim 1, which relates to the preparation of compounds of the formula (9) in which m is 2.

10. A process according to claim 1, which relates to the preparation of compounds of the formula (9) in which m is 1.

11. A process according to claim 1, which relates to the preparation of the compound of the formula (10)

12. A process according to claim 1, which relates to the preparation of the compound of the formula (11)

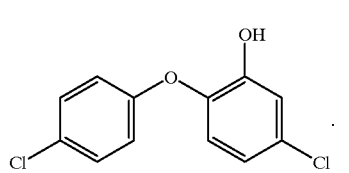

13. A process according to claim 1, wherein the oxidation is carried out in the presence of a mixture of a mixture of acetic anhydride, sulfuric acid and $H_2O_2$.

* * * * *